United States Patent [19]

Bradford et al.

[11] Patent Number: Plant 6,407

[45] Date of Patent: Nov. 22, 1988

[54] CHERRY TREE, "TULARE"

[76] Inventors: Norman G. Bradford, 11875 E. Savana Rd.; Lowell G. Bradford, 12439 E. Savana Rd., both of LeGrand, Calif. 95333

[21] Appl. No.: 12,648

[22] Filed: Feb. 9, 1987

[51] Int. Cl.[4] ..... A01H 5/00

[52] U.S. Cl. ..... Plt./37

[58] Field of Search ..... Plt./37

[56] References Cited

U.S. PATENT DOCUMENTS

P.P. 5,478 5/1985 Anderson ..... Plt. 37

*Primary Examiner*—James R. Feyrer

*Attorney, Agent, or Firm*—Worrel & Worrel

[57] ABSTRACT

A new and distinct variety of cherry tree which is characterized by a date of maturity of approximately May 19 through May 23 under the ecological conditions prevailing at LeGrand, Calif., which is approximately three days prior to the King Cherry Tree of U.S. Plant Pat. No. 5,478, and the Bing Cherry Tree (unpatented) with which it is most closely similar, and which it is further distinguished as to novelty by producing a cherry which has exceptional storage and shipping characteristics.

1 Drawing Sheet

BACKGROUND OF THE NEW VARIETY

The present invention relates to a new and distinct variety of cherry tree which has been denominated varietally as "Tulare", and more particularly to such a cherry tree which is closely similar in physical characteristics to the "King Cherry Tree" (U.S. Plant Pat. No. 5,478) and the "Bing" variety of cherry tree (unpatented), but which is distinguished therefrom in the production of fruit which is ripe for harvesting approximately three days earlier than the King Cherry Tree and ten days earlier than the Bing Cherry Tree, and which furthermore produces fruit which is virtually non-doubling, firm and has excellent storage and shipping characteristics.

In a continuing effort to upgrade the quality of their fruit, the inventors are constantly on the alert to locate any new varieties that may appear as chance randomly cross-pollinated seedlings and mutations in their experimental orchard. In these labors, the applicants in 1974 discovered an open pollinated seedling which originated from a second generation seedling of a Bing Cherry Tree (unpatented) in the cultivated area of their experimental orchard which is located at 9766 E. Mariposa Way, LeGrand, Calif. in the County of Merced.

ORIGIN AND ASEXUAL REPRODUCTION OF THE NEW VARIETY

The present variety of cherry tree was an open pollinated seedling of an unnamed seedling which was an open pollinated Bing Cherry Tree (unpatented) which was discovered within the experimental orchard under the ownership and control of the inventors at 9766 E. Mariposa Way, LeGrand, Calif. The subject variety was observed at that time to have desirable characteristics and it was thereafter asexually reproduced by the inventors at the same orchard by budding and grafting from the original open pollinated seedling onto positions on test trees for the purpose of determining whether the fruit characteristics were true to the original seedling. This first asexual propagation which occurred in 1974, has been continually observed by the inventors and it has been subsequently determined that the progeny produced possessed the same distinctive characteristics as the original open pollinated seedling.

The cherry tree of the present invention is noteworthy in ripening approximately ten days earlier than the Bing Cherry Tree (unpatented), and three days earlier than the King Cherry Tree (U.S. Plant Pat. No. 5,478), with which it is most closely similar, but which is distinguished therefrom by producing fruit which grows well under the ecological conditions prevailing in the San Joaquin Valley of Central California and which further has the desirable characteristics of being virtually non-doubling, extremely firm, and having an excellent flavor.

BRIEF DESCRIPTION OF THE DRAWING

The accompanying drawing is a color photograph of a characteristic twig bearing typical leaves; a bunch of cherries showing their external coloration sufficiently matured for harvesting and shipment; two cherries, one dissected in the axial plane and the other halved transversely of the suture plane to illustrate the flesh coloration, and the stone coloration, all of the subject variety.

DETAILED DESCRIPTION

Referring more specifically to the pomological details of this new and distinct variety of cherry tree, the following has been observed under the ecological conditions prevailing at the orchard of the inventors located in LeGrand, Calif. All major color code designations are by reference to the Inter-Society Color Council, National Bureau of Standards. Common color names are also used occasionally.

TREE

Size:

*Generally.*—Medium.

Vigor: Average.

Figure: Upright, open, and vase formed.

Productivity: Productive; half hardy under typical Central San Joaquin Valley climatic conditions.

Regularity of bearing: Regular.

Trunk:

*Size.*—Generally — medium.

*Bark texture.*—Average.
*Bark color.*—Grayish brown, [61 gy. Br.].
*Lenticels — numbers.*—Numerous.
*Lenticels — size.*—Large, approximately $\frac{1}{8}''$ to $\frac{1}{4}''$, [3.175–6.35 mm.].
*Lenticels — color.*—Brown.

BRANCHES

Size:
*Generally.*—Medium.
Texture: Average.
*Color — first year wood.*—Brownish red, [43 m.r. Br.].
*Color — second year wood.*—A dull grey, [61 gy. Br.].
Lenticels:
*Numbers.*—Numerous.
*Size.*—Small, approximately 1/16" to $\frac{1}{8}''$, [1.588–3.175 mm.].
*Color.*—Brown.

LEAVES

Size:
*Generally.*—Average.
*Length.*—Approximately $5\frac{1}{2}''$, [139.7 mm.].
*Width.*—Approximately $2\frac{1}{4}''$, [57.15 mm.].
Leaf form:
*Generally.*—Elliptical.
Apex:
*Shape.*—Slightly aristate.
Base:
*Shape.*—Acute.
Thickness: Average.
Leaf texture: Glabrous.
Color:
*Dorsal surface.*—Dark Green, [125. m. 01 G].
*Ventral surface.*—Light green, [122. gy. YG].
Vanes:
*Generally.*—Pinnately, net veined.
Marginal form:
*Generally.*—Serrate.
Petiole:
*Length.*—Average; approximately $1\frac{3}{8}''$, [34.925 mm.].
*Thickness.*—Average, approximately 1/16" in diameter, [1.588 mm.].
Glands:
*Numbers.*—Two glands appear on each stem.
*Position.*—Alternate; the glands appear on the stem at a position approximately $\frac{1}{4}''$ [6.35 mm.] from the leaf blade.
*Size.*—Average.
*Form.*—Reniform.
*Color*—Red, [approximately 15. m Red.].
*Stipules — Generally.*—Present.
*Stipules — Numbers.*—Few.
*Stipules — Length.*—Approximately $\frac{1}{4}''$, [6.35 mm.].
Leaf buds:
*Generally.*—Pointed.
Flower buds:
*Generally.*—Half hardy under typical San Joaquin Valley climatic conditions.
*Size.*—Generally — Average.
*Length.*—Medium.
*Form.*—Obtuse, free and glabrous.
Flowers:
*Generally.*—Self-sterile; the Cherry Tree variety "Tulare" must be cross-pollinated to produce fruit. At the present time the King Cherry tree (U.S. Plant Pat. No. 5,478) appears to be the most likely pollinator. The two varieties have been tested together and it appears that they compliment each other both in terms of pollination and for harvesting convenience.

Date of first bloom: In 1986, the first bloom was Feb. 24, 1986, however, 1986 was an exceptional season. It is estimated that the 1986 bloom date was 14 to 18 days prior to the normal bloom date for the subject variety.

Date of full bloom: Mar. 1, 1986. This date similarly is estimated to be 14 to 18 days earlier than the date for a typical season for the subject variety.
*Blossom size.*—Generally — average.
*Blossom color.*—White [263 white].
*Date of bloom.*—Generally — early as compared with other varieties.

FRUIT

Maturity when described, ripe for harvest: Approximately May 5 in 1986. It should be understood that the date of harvest was approximately 14 to 18 days earlier in 1986 due to the exceptional environmental conditions prevailing in 1986. It should be appreciated, therefore, that the variety would normally be mature for harvest between May 19 and May 23 at LeGrand, Calif.
Size:
*Generally.*—Average.
Uniformity: Uniform.
Average diameter in the axial plane: Approximately 15/16", [23.812 mm.].
Average diameter in suture plane: Approximately 13/16", [20.638 mm.].
Average diameter in the cheek plane: Approximately 1 1/16", [26.988 mm.].
Form:
*Generally.*—Slightly oblong, and somewhat slightly compressed toward the suture.
*Form — longitudinal section.*—Slightly oblong.
*Form — cheek plane.*—Oblate.
Symmetry: Symmetrical.
Suture: The suture appears as an inconspicuous line which extends from the base toward, but discontinues at, the apex. The suture has a slight depression somewhat slightly beyond the pistil point.
Ventral surface:
*Form.*—Rounded slightly.
Stem cavity:
*Form.*—Flaring and somewhat circular with the suture appearing on one side.
*Depth.*—Approximately $\frac{1}{8}''$, [3.175 mm.].
*Width.*—Approximately 1/16", [1.588 mm.].
Base:
*Form.*—Cuneate; occasionally the base appears truncated.
Apex:
*Generally.*—Rounded.
*Pistil point.*—Pistil point appears as an almost inconspicuous dot.
Stem:
*Size.*—Medium.
*Length.*—Approximately $1\frac{3}{8}''$ [34.925 mm.].
*Width.*—Approximately 1/16", [1.588 mm.].
Skin:
*Thickness.*—Average.
*Texture.*—Medium.

Tenacious to flesh: Yes.
Tendency to crack: Not observed.
Skin color: Dark red, [13 Deep Red].
Flesh:
*Color.*—Variable from red to pink, commonly a slight pink, [3. deep Pink.].
Fibers:
*Numbers.*—Abundant.
*Texture.*—Fine.
*Color.*—White.
Surface of pit cavity:
*Color.*—Dark red, [13. deep Red.].
Amygdalin: Wanting.
Juice production: Abundant.
Texture: Very firm.
Ripening: Even.
Flavor: Sweet, although mildly acidic.
Aroma: Pronounced.
Eating quality: Noteworthy.
Stone: Semi-Freestone. The stone adheres to the flesh along both the dorsal and the ventral edges.
*Form.*—Obvoid.
*Base.*—Slightly oblique.
*Hilum.*—Oval.
*Apex.*—Rounded, occasionally slightly acute.
*Surface texture.*—Smooth.
*Sides.*—Generally — equal.
*Size.*—Generally — Medium.
Average stone length: Approximately 7/16", [11.112 mm.].
Average stone width: Approximately 5/16", [7.938 mm.].
Average stone thickness: Approximately 3/16", [4.762 mm.].
Color of stone: Light brown, [57 1. Br.].
Thickness of pit wall:
*Generally.*—Thin, approximately 1/64", [0.397 mm.].

Tendency to split: Not observed.
Kernel:
*Form.*—Oval.
Flavor of kernel: Bitter.
*Viability.*—Yes.
*Ventral edge.*—Appears as a broadly flattened ridge.
*Dorsal edge.*—Acute, with no fin.
Use: Fresh market; for both local and long distance markets.
Shipping quality: Noteworthy.
Keeping quality: Exceptional.
Resistance to diseases and insects: No particular susceptibilities were noted.

Although the new variety of cherry tree possesses the described characteristics when grown under the conditions prevailing in LeGrand, Calif., in the central part of the San Joaquin Valley, it is to be understood that variations in the usual magnitude and characteristics incident to changes in growing conditions, fertilization, pruning and pest control are to be expected.

Having thus described and illustrated our new variety of cherry tree, we claim:

1. A new and distinct variety of cherry tree substantially as illustrated and described which is somewhat similar to the King Cherry Tree (U.S. Plant Pat. No. 5,478) and the Bing Cherry tree (unpatented), which it most closely resembles, but from which it is distinguished therefrom by bearing fruit which are a uniform and full dark red color, which ripens approximately three days earlier than the King Cherry Tree (U.S. Plant Pat. No. 5,478) and ten days earlier than the Bing Cherry Tree (unpatented) at LeGrand, Calif., and which further has displayed the desirable traits of being virtually non-doubling, and having exceptional handling and shipping characteristics.

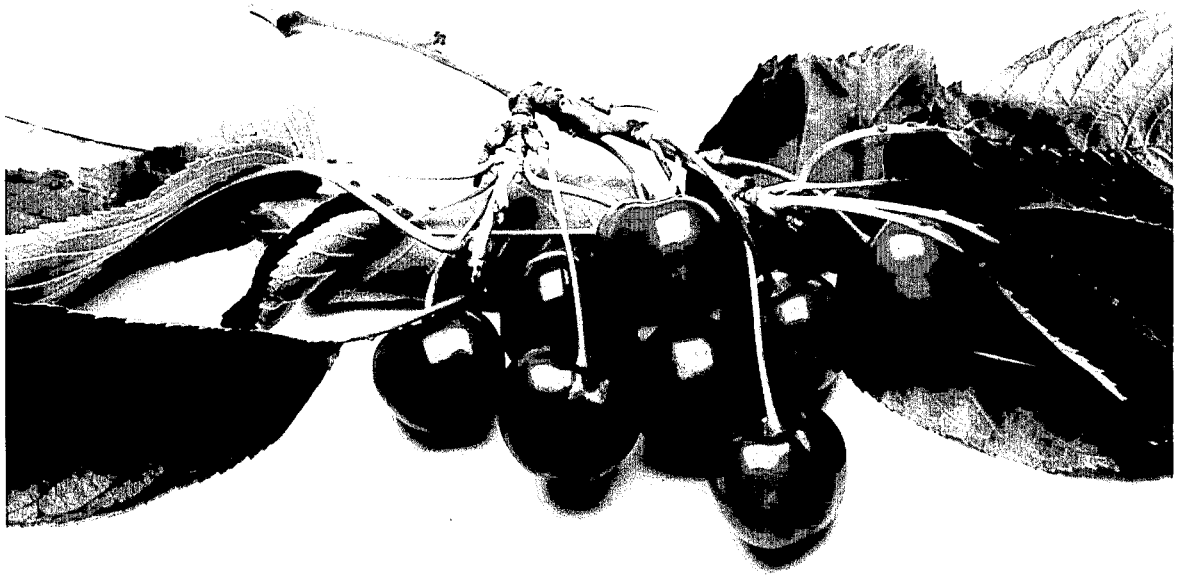
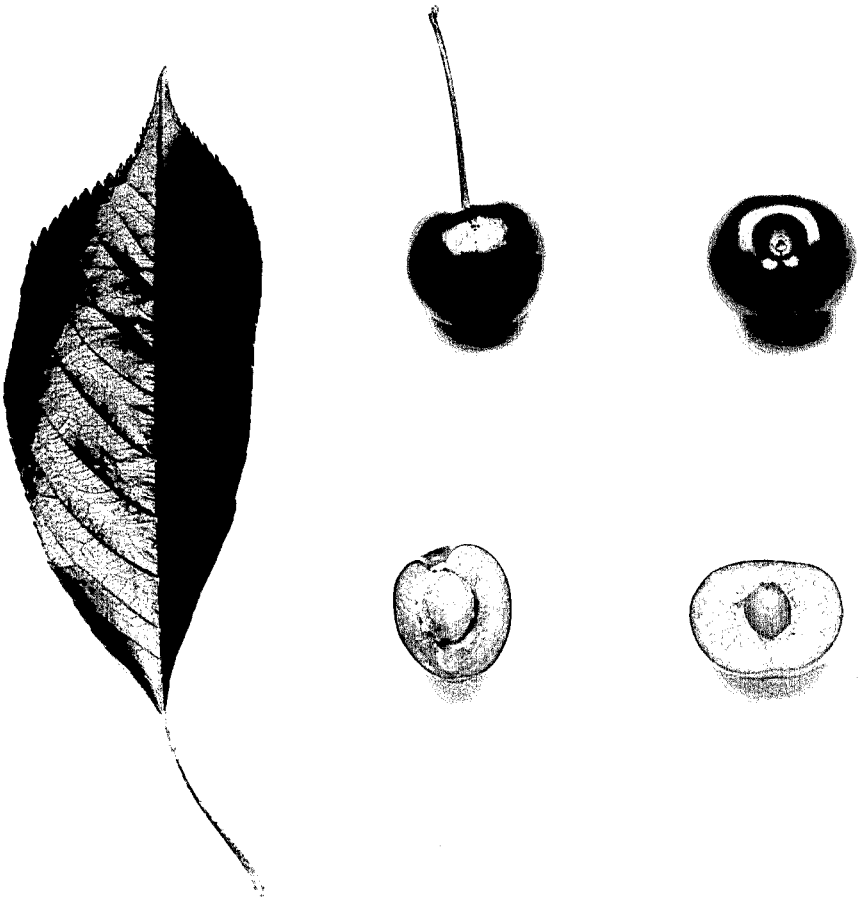

* * * * *